(12) United States Patent
Christie et al.

(10) Patent No.: US 6,291,223 B1
(45) Date of Patent: Sep. 18, 2001

(54) MOUSE ASPARTIC SECRETASE-1 (MASP1)

(75) Inventors: Gary Christie, Harlow (GB); Xiaotong Li, Devon, PA (US); David J. Powell, Harlow (GB); Yuan Zhu, Blue Bell, PA (US)

(73) Assignees: SmithKline Beecham Corporation, Philadelphia, PA (US); SmithKline Beecham plc, Brentford (GB)

( * ) Notice: Subject to any disclaimer, the term of this patent is extended or adjusted under 35 U.S.C. 154(b) by 0 days.

(21) Appl. No.: 09/717,432

(22) Filed: Nov. 21, 2000

Related U.S. Application Data

(60) Provisional application No. 60/166,974, filed on Nov. 23, 1999.

(51) Int. Cl.$^7$ ................ C12N 9/48; C12N 1/20; C12N 9/50; C12N 5/06; C07H 21/04
(52) U.S. Cl. ............ 435/212; 435/219; 435/252.3; 435/320.1; 435/325; 435/354; 536/23.2
(58) Field of Search ................ 435/212, 219, 435/252.3, 320.1, 354, 325; 536/23.2

(56) References Cited

U.S. PATENT DOCUMENTS 6,025,180  2/2000  Powell et al. .............. 435/219

FOREIGN PATENT DOCUMENTS

848062 A2  6/1998  (EP) .
WO 99/33963 A1  7/1999  (WO) .

OTHER PUBLICATIONS

GenBank Accession No. AF050171, Accarino, et al., Submitted (Feb. 24, 1998).

GenBank Accession No. AU080335, Hashimoto, et al., Last updated Jul. 12, 2000.

GenBank Accession No. AF051150, Accarino et al., Submitted (Feb. 25, 1998).

GenBank Accession No AF117892, Xin, et al., Submitted (Jan. 5, 1999).

Xin, et al., "Identification of a novel aspartic–like protease differentially expressed in human breast cancer cell lines", Biochimica et Biophysica Acta , vol. 1501, pp. 125–137 (2000).

GenBank Accession No. AF216310, Choi, et al., Feb. 29, 2000.

Vassar, et al., "Beta–Secretase Cleavage of Alzheimer's Amyloid Precursor Protein by the Transmembrane Aspartic Protease BACE", Science vol. 286, pp. 735–741 (1999).

Hussain, et al., "Indentification of a Novel Aspartic Protease (Asp 2) as Beta–Secretase", Molecular and Cellular Neuroscience, vol. 14, pp. 419–427 (1999).

Yan, et al., "Membrane–anchored aspartyl protease with Alzheimer's disease Beta–secretase activity", Nature, vol. 402, pp. 533–537 (1999).

*Primary Examiner*—Elizabeth Slobodyansky
*Assistant Examiner*—Yong Pak
(74) *Attorney, Agent, or Firm*—Elizabeth J. Hecht; Ratner & Prestia; William T. King

(57) ABSTRACT

Mouse mASP1 polypeptides and polynucleotides and method for producing such polypeptides by recombinant techniques are disclosed. Also disclosed are methods for screening for compounds that either agonize or antagonize mouse mASP1. Such compounds are expected to be useful in treatment of human diseases, including, but not limited to: Alzheimer's disease, cancer, and prohormone processing.

8 Claims, No Drawings

MOUSE ASPARTIC SECRETASE-1 (MASP1)

RELATED APPLICATIONS

This application claims priority of U.S. Provisional Application Ser. No. 60/166,974, filed on Nov. 23, 1999.

FIELD OF THE INVENTION

This invention relates to newly identified polypeptides and polynucleotides encoding such polypeptides, to their use in identifying compounds that may be agonists and/or antagonists that are potentially useful in therapy, and to production of such polypeptides and polynucleotides.

BACKGROUND OF THE INVENTION

The drug discovery process is currently undergoing a fundamental revolution as it embraces "functional genomics," that is, high throughput genome- or gene-based biology. This approach is rapidly superseding earlier approaches based on 'positional cloning'. A phenotype, that is a biological function or genetic disease, would be identified and this would then be tracked back to the responsible gene, based on its genetic map position.

Functional genomics relies heavily on the various tools of bioinformatics to identify gene sequences of potential interest from the many molecular biology databases now available. There is a continuing need to identify and characterise further genes and their related polypeptides/proteins, as targets for drug discovery.

There are currently five known human aspartic proteases (or proteinases), namely, pepsin, gastricsin, cathespin D, cathespin E and renin, and these have widely varying functions. Pepsin and gastricsin are involved in nutritive processes in the stomach; cathepsin D is involved in protein turnover in many cell types; and renin has the highly specific function of angiotensin production from its precursor form, angiotensinogen. The precise role of cathepsin E remains to be confirmed, although its location in some epithelial cell types has indicated a role in antigen processing. It may also be involved in certain inflammatory conditions, such as *Helicobacter pylori* infection in the stomach. This indicates that the Aspartic Proteinase family has an established, proven history as therapeutic targets. Clearly there is a need for identification and characterisation of further members of the Aspartic Proteinase family which can play a role in preventing, ameliorating or correcting dysfunctions or diseases, including, but not limited to, Alzheimer's Disease, cancer, and prohormone processing.

SUMMARY OF THE INVENTION

The present invention relates to mouse mASP1, in particular mouse mASP1 polypeptides and mouse mASP1 polynucleotides, recombinant materials and methods for their production. In another aspect, the invention relates to methods for identifying agonists and antagonists/inhibitors of the mouse mASP1 gene. This invention further relates to the generation of in vitro and in vivo comparison data relating to the polynucleotides and polypeptides in order to predict oral absorption and pharmacokinetics in man of compounds that either agonize or antagonize the biological activity of such polynucleotides or polypeptides. Such a comparison of data will enable the selection of drugs with optimal pharmacokinetics in man, ie., good oral bioavailability, blood-brain barrier penetration, plasma half life, and minimum drug interaction.

The present invention further relates to methods for creating transgenic animals, which overexpress or underexpress or have regulatable expression of a mASP1 gene and "knock-out" animals, preferably mice, in which an animal no longer expresses a mASP1 gene. Furthermore, this invention relates to transgenic and knock-out animals obtained by using these methods. Such animal models are expected to provide valuable insight into the potential pharmacological and toxicological effects in humans of compounds that are discovered by the aforementioned screening methods as well as other methods. An understanding of how a mouse mASP1 gene functions in these animal models is expected to provide an insight into treating and preventing human diseases including, but not limited to: Alzheimer's disease, cancer, and prohormone processing, hereinafter referred to as "the Diseases," amongst others.

DESCRIPTION OF THE INVENTION

In a first aspect, the present invention relates to mouse mASP1 polypeptides. Such polypeptides include isolated polypeptides comprising an amino acid sequence having at least a 95% identity, most preferably at least a 97–99% identity, to that of SEQ ID NO: 2 over the entire length of SEQ ID NO: 2. Such polypeptides include:

(a) an isolated polypeptide comprising the amino acid of SEQ ID NO: 2;

(b) an isolated polypeptide encoded by a polynucleotide comprising the sequence contained in SEQ ID NO: 1;

(c) an isolated polypeptide comprising a polypeptide sequence having at least a 95%, 97%, 98%, or 99% identity to the polypeptide sequence of SEQ ID NO: 2;

(d) an isolated polypeptide having at least a 95%, 97%, 98%, or 99% identity to the polypeptide sequence of SEQ ID NO: 2;

(e) the polypeptide sequence of SEQ ID NO: 2; and (f) variants and fragments thereof; and portions of such polypeptides in (a) to (e) that generally contain at least 30 amino acids, more preferably at least 50 amino acids, thereof.

Polypeptides of the present invention are believed to be members of the aspartic protease (proteinase) family of polypeptides. They are, therefore, of interest, because the Aspartic Proteinase family has an established, proven history as therapeutic targets. Furthermore, the polypeptides of the present invention can be used to establish assays to predict oral absorbtion and pharmacokinetics in man and thus enhance compound and formulation design, among others. These properties, either alone or in the aggregate, are hereinafter referred to as "mouse mASP1 activity" or "mouse mASP1 polypeptide activity" or "biological activity of mASP1." Preferably, a polypeptide of the present invention exhibits at least one biological activity of mouse mASP1.

Polypeptides of the present invention also include variants of the aforementioned polypeptides, including alleles and splice variants. Such polypeptides vary from the reference polypeptide by insertions, deletions, and substitutions that may be conservative or non-conservative. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination. Particularly preferred primers will have between 20 and 25 nucleotides.

Preferred fragments of polypeptides of the present invention include an isolated polypeptide comprising an amino acid sequence having at least 15, 20, 30, 40, 50 or 100 contiguous amino acids from the amino acid sequence of SEQ ID NO: 2, or an isolated polypeptide comprising an amino acid sequence having at least 15, 20, 30, 40, 50 or 100 contiguous amino acids truncated or deleted from the amino acid sequence of SEQ ID NO: 2.

Also preferred are biologically active fragments that mediate activities of mASP1, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of mouse or the ability to initiate, or maintain cause the Diseases in an individual, particularly a human.

Fragments of the polypeptides of the invention may be employed for producing the corresponding full-length polypeptide by peptide synthesis; therefore, these variants may be employed as intermediates for producing the full-length polypeptides of the invention.

The polypeptides of the present invention may be in the form of a "mature" protein or may be a part of a larger protein such as a fusion protein. It is often advantageous to include an additional amino acid sequence that contains secretory or leader sequences, pro-sequences, sequences that aid in purification, for instance, multiple histidine residues, or an additional sequence for stability during recombinant production.

The present invention also includes variants of the aforementioned polypeptides, that is polypeptides that vary from the referents by conservative amino acid substitutions, whereby a residue is substituted by another with like characteristics. Typical substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to mouse mASP1 polynucleotides. Such polynucleotides include isolated polynucleotides comprising a nucleotide sequence encoding a polypeptide having at least a 95% identity, to the amino acid sequence of SEQ ID NO: 2, over the entire length of SEQ ID NO: 2. In this regard, polypeptides which have at least a 97% identity are highly preferred, while those with at least a 98–99% identity are more highly preferred, and those with at least a 99% identity are most highly preferred. Such polynucleotides include a polynucleotide comprising the nucleotide sequence contained in SEQ ID NO: 1 encoding the polypeptide of SEQ ID NO: 2.

Further polynucleotides of the present invention include isolated polynucleotides comprising a nucleotide sequence having at least a 95% identity, to a nucleotide sequence encoding a polypeptide of SEQ ID NO: 2, over the entire coding region. In this regard, polynucleotides which have at least 97% identity are highly preferred, while those with at least a 98–99% identity are more highly preferred, and those with at least a 99% identity are most highly preferred.

Further polynucleotides of the present invention include isolated polynucleotides comprising a nucleotide sequence having at least a 95% identity, to SEQ ID NO: I over the entire length of SEQ ID NO: 1. In this regard, polynucleotides which have at least a 97% identity are highly preferred, while those with at least a 98–99% identify are more highly preferred, and those with at least a 99% identity are most highly preferred. Such polynucleotides include a polynucleotide comprising the polynucleotide of SEQ ID NO: 1, as well as the polynucleotide of SEQ ID NO: 1.

The invention also provides polynucleotides that are complementary to all the above described polynucleotides.

The nucleotide sequence of SEQ ID NO: 1 shows homology with human aspartic-like protease (GenBank Accession No. AF117892, Xin, H., et al.) and human aspartyl protease (GenBank Accession No. AF050171, Accarino, M. P., et al.). The nucleotide sequence of SEQ ID NO: 1 is a cDNA sequence and comprises a polypeptide encoding sequence (nucleotide 1 to 1545) encoding a polypeptide of 514 amino acids, the polypeptide of SEQ ID NO: 2. The nucleotide sequence encoding the polypeptide of SEQ ID NO: 2 may be identical to the polypeptide encoding sequence of SEQ ID NO: 1 or it may be a sequence other than SEQ ID NO: 1, which, as a result of the redundancy (degeneracy) of the genetic code, also encodes the polypeptide of SEQ ID NO: 2. The polypeptide of SEQ ID NO: 2 is structurally related to other proteins of the aspartic protease family, having homology and/or structural similarity with human aspartic-like protease (GenBank Accession No. AF117892, Xin, H., et al.) and human aspartyl protease (GenBank Accession No. AF050171, Accarino, M. P., et al.).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one mASP1 activity.

Polynucleotides of the present invention may be obtained, using standard cloning and screening techniques, from a cDNA library derived from mRNA in cells of mouse kidney, using the expressed sequence tag (EST) analysis (Adams, M. D., et al. *Science* (1991) 252:1651–1656; Adams, M. D. et al., *Nature* (1992) 355:632–634; Adams, M. D., et al., *Nature* (1995) 377 Supp.: 3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro- protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz, et al., *Proc Natl Acad Sci USA* (1989) 86:821–824, or is an HA tag. The polynucleotide may also comprise non-coding 5' and 3' sequences, such as transcribed, non-translated sequences, splicing and polyadenylation signals, ribosome binding sites and sequences that stabilize MRNA.

Further embodiments of the present invention include polynucleotides encoding polypeptide variants that comprise the amino acid sequence of SEQ ID NO: 2 and in which several, for instance from 50 to 30, from 30 to 20, from 20 to 10, from 10 to 5, from 5 to 3, from 3 to 2, from 1 to 1 or I amino acid residues are substituted, deleted or added, in any combination. Particularly preferred probes will have between 30 and 50 nucleotides, but may have between 100 and 200 contiguous nucleotides of the polynucleotide of SEQ ID NO: 1.

A preferred embodiment of the invention is a polynucleotide consisting of or comprising nucleotide 1 to the nucleotide immediately upstream of or including nucleotide 1545 set forth in SEQ ID NO: 1, both of which encode a mASP1 polypeptide.

The invention also includes a polynucleotide consisting of or comprising a polynucleotide of the formula:

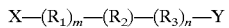

$$X—(R_1)_m—(R_2)—(R_3)_n—Y$$

wherein, at the 5' end of the molecule, X is hydrogen, a metal or a modified nucleotide residue, or together with Y defines a covalent bond, and at the 3' end of the molecule, Y is hydrogen, a metal, or modified nucleotide residue, or together with X defines the covalent bond, each occurrence of $R_1$ and $R_3$ is independently any nucleic acid residue or modified nucleic acid residue, m is an integer between 1 and 3000 or zero, n is an integer between 1 and 3000 or zero, and $R_2$ is a nucleic acid sequence or modified nucleic acid sequence of the invention, particularly the nucleic acid sequence set forth in SEQ ID NO: 1 or a modified nucleic acid sequence thereof. In the polynucleotide formula above, $R_2$ is oriented so that its 5' end nucleic acid residue is at the left, bound to $R_1$, and its 3' end nucleic acid residue is at the right, bound to $R_3$. Any stretch of nucleic acid residues denoted by either $R_1$ and/or $R_2$, where m and/or n is greater than 1, may be either a heteropolymer or a homopolymer, preferably a heteropolymer. Where, in a preferred embodiment, X and Y together define a covalent bond, the polynucleotide of the above formula is a closed, circular polynucleotide, which can be a double-stranded polynucleotide wherein the formula shows a first strand to which the second strand is complementary. In another preferred embodiment m and/or n is an integer between 1 and 1000. Other preferred embodiments of the invention are provided where m is an integer between 1 and 50, 100 or 500, and n is an integer between 1 and 50, 100, or 500.

Polynucleotides that are identical, or are substantially identical to a nucleotide sequence of SEQ ID NO: 1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding homologs and orthologs from species other than mouse) that have a high sequence identity to SEQ ID NO: 1. Typically these nucleotide sequences are 95% identical to that of the referent. Preferred probes or primers will generally comprise at least 15 nucleotides, preferably, at least 30 nucleotides and may have at least 50 nucleotides, and may even have at least 100 nucleotides. Particularly preferred primers will have between 20 and 25 nucleotides.

A polynucleotide encoding a polypeptide of the present invention, including homologs and orthologs from a species other than mouse, may be obtained by a process comprising the steps of screening an appropriate library under stringent hybridization conditions with a labeled probe having the sequence of SEQ ID NO: 1 or a fragment thereof, preferably of at least 15 nucleotides in length; and isolating full-length cDNA and genomic clones comprising said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA; followed by washing the filters in 0.1×SSC at about 65° C. Thus, the present invention also includes isolated polynucleotides, preferably of at least 100 nucleotides in length, obtained by screening an appropriate library under stringent hybridization conditions with a labeled probe having the sequence of SEQ ID NO: 1 or a fragment thereof, preferably of at least 15 nucleotides.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the MRNA template during 1 st strand cDNA synthesis.

There are several methods available and well known to those skilled in the art to obtain full-length cDNAs, or extend short cDNAs, for example, those based on the method of Rapid Amplification of cDNA ends (RACE) (see, for example, Frohman, et al., *Proc. Natl. Acad. Sci., USA* 85, 8998–9002, 1988). Recent modifications of the technique, exemplified by the Marathon™ technology (Clontech Laboratories Inc.), for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis, et al., BASIC METHODS IN MOLECULAR BIOLOGY (1986) and Sambrook, et al., MOLECULAR CLONING: A LABORATORY MANUAL, 2nd Ed., Cold Spring Harbor Laboratory Press, Cold Spring Harbor, N.Y. (1989). Preferred methods of introducing polynucleotides into host cells include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli, Streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may comprise control regions that regulate as well as engender expression. Generally, any system or vector that is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook, et al., MOLECULAR CLONING, A LABORATORY MANUAL (supra).

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and/or purification.

The polynucleotide sequences of the present invention are also valuable for chromosome localization studies. The polynucleotide sequence, or fragment(s) thereof, is specifically targeted to, and can hybridize with, a particular location on an individual human chromosome. The mapping of these sequences to human chromosomes according to the present invention is an important first step in correlating homologous human polynucleotide sequences with gene associated disease in humans.

Precise chromosomal localizations for a polynucleotide sequence (gene fragment, etc.) can be determined using Radiation Hybrid (RH) Mapping (Walter, M., et al. (1994) *Nature Genetics* 7, 22–28), for example. A number of RH panels are available, including mouse, rat, baboon, zebrafish and human. RH mapping panels are available from a number of sources, for example Research Genetics (Huntsville, Ala., USA). To determine the chromosomal location of a polynucleotide sequence using these panels, PCR reactions are performed using primers, designed to the polynucleotide sequence of interest, on the RH DNAs of the panel. Each of these DNAs contains random genomic fragments from the species of interest. These PCRs result in a number of scores, one for each RH DNA in the panel, indicating the presence or absence of the PCR product of the polynucleotide sequence of interest. These scores are compared with scores created using PCR products from genomic sequences of known location, usually using an on-line resource such as that available at the Whitehead Institute for Biomedical Research in Cambridge, Mass., USA website (http://www.genome.wi.mit.edu/). Once a polynucleotide sequence has been mapped to a precise chromosomal location, the physical position of the sequence on the chromosome can be correlated with genetic map data for that species. Also, as a consequence of synteny, where knowledge of the position of a gene on a chromosome of one species can be used to determine the likely position of the orthologous gene on the chromosome of another species, this knowledge can then be used to identify candidate genes for human disease. Thus the localization of a polynucleotide sequence of interest to a specific mouse chromosomal location can be used to predict the localization of the orthologous human gene on the corresponding human chromosome. From this data, potential disease association may be inferred from genetic map sources such as, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes Mouse mASP1 gene products can be expressed in transgenic animals. Animals of any species, including, but not limited to: mice, rats, rabbits, guinea pigs, dogs, cats, pigs, micro-pigs, goats, and non-human primates, e.g., baboons, monkeys, chimpanzees, may be used to generate mASP1 transgenic animals.

This invention further relates to a method of producing transgenic animals, preferably mouse, over-expressing mASP1, which method may comprise the introduction of several copies of a segment comprising at least the polynucleotide sequence encoding SEQ ID NO: 2 with a suitable promoter into the cells of a mouse embryo, or the cells of another species, at an early stage.

This invention further relates to a method of producing transgenic animals, preferably mouse, under-expressing or regulatably expressing mASP1, which method may comprise the introduction of a weak promoter or a regulatable promoter (e.g., an inducible or repressible promoter) respectively, expressibly linked to the polynucleotide sequence of SEQ ID NO: 1 into the cells of a mouse embryo at an early stage.

This invention also relates to transgenic animals, characterized in that they are obtained by a method, as defined above.

Any technique known in the art may be used to introduce a mouse mASP1 transgene into animals to produce a founder line of animals. Such techniques include, but are not limited to: pronuclear microinjection (U.S. Pat. No. 4,873, 191); retrovirus mediated gene transfer into germ lines (Van der Putten, et al., *Proc. Natl. Acad. Sci., USA* 82: 6148–6152 (1985); gene targeting in embryonic stem cells (Thompson, et al., *Cell* 56: 313–321 (1989); electropolation of embryos (Lo, *Mol. Cell Biol.* 3: 1803–1814 (1983); and sperm-mediated gene transfer (Lavitrano, et al., *Cell* 57: 717–723 (1989); etc. For a review of such techniques, see Gordon, *Intl. Rev. Cytol.* 115: 171–229 (1989).

A further aspect of the present invention involves gene targeting by homologous recombination in embryonic stem cells to produce a transgenic animal with a mutation in a mASP1 gene ("knockout" mutation). In such so-called "knock-out" animals, there is inactivation of the mASP1 gene or altered gene expression, such that the animals are useful to study the function of the mASP1 gene, thus providing animals models of human disease, which are otherwise not readily available through spontaneous, chemical or irradiation mutagenesis. Another aspect of the present invention involves the generation of so-called "knock-in" animals in which a portion of a wild-type gene is fused to the cDNA of a heterologous gene.

This invention further relates to a method of producing "knock-out" animals, preferably mice, no longer expressing mASP1. By using standard cloning techniques, a mouse mASP1 cDNA (SEQ ID NO: 1) can be used as a probe to screen suitable libraries to obtain the murine mASP1 genomic DNA clone. Using the murine genomic clone, the method used to create a knockout mouse is characterized in that:

- a suitable mutation is produced in the polynucleotide sequence of the murine mASP1 genomic clone, which inhibits the expression of a gene encoding murine mASP1, or inhibits the activity of the gene product;
- said modified murine mASP1 polynucleotide is introduced into a homologous segment of murine genomic DNA, combined with an appropriate marker, so as to obtain a labeled sequence comprising said modified murine genomic DNA;
- said modified murine genomic DNA comprising the modified polynucleotide is transfected into embryonic stem cells and correctly targeted events selected in vitro; then
- said stem cells are reinjected into a mouse embryo; then
- said embryo is implanted into a female recipient and brought to term as a chimera which transmits said mutation through the germline; and
- homozygous recombinant mice are obtained at the F2 generation which are recognizable by the presence of the marker.

Various methods for producing mutations in non-human animals are contemplated and well known in the art. In a preferred method, a mutation is generated in a murine mASP1 allele by the introduction of a DNA construct comprising DNA of a gene encoding murine mASP1, which murine gene contains the mutation. The mutation is targeted to the allele by way of the DNA construct. The DNA of the gene encoding murine mASP1 comprised in the construct may be foreign to the species of which the recipient is a member, may be native to the species and foreign only to the individual recipient, may be a construct comprised of synthetic or natural genetic components, or a mixture of these. The mutation may constitute an insertion, deletion, substitution, or combination thereof. The DNA construct can be introduced into cells by, for example, calcium-phosphate DNA co-precipitation. It is preferred that a mutation be introduced into cells using electroporation, microinjection, virus infection, ligand-DNA conjugation, virus-ligand-DNA conjugation, or liposomes.

Another embodiment of the instant invention relates to "knock-out" animals, preferably mice, obtained by a method of producing recombinant mice as defined above, among others.

Another aspect of this invention provides for in vitro mASP1 "knock-outs", i.e., tissue cultures. Animals of any species, including, but not limited to: mice, rats, rabbits, guinea pigs, dogs, cats, pigs, micro-pigs, goats, and non-human primates, e.g., baboons, monkeys, chimpanzees, may be used to generate in vitro mASP1 "knock-outs". Methods for "knocking out" genes in vitro are described in Galli-Taliadoros, et al., *Journal of Immunological Methods* 181: 1–15 (1995).

Transgenic, "knock-in", and "knock-out" animals, as defined above, are a particularly advantageous model, from a physiological point of view, for studying aspartic protease. Such animals will be valuable tools to study the functions of a mASP1 gene. Moreover, such animal models are expected to provide information about potential toxicological effects in humans of any compounds discovered by an aforementioned screening method, among others. An understanding of how a mouse mASP1 gene functions in these animal models is expected to provide an insight into treating and preventing human diseases including, but not limited to: Alzheimer's disease, cancer, and prohormone processing.

Polypeptides of the present invention are responsible for many biological functions, including many disease states, in particular the Diseases mentioned herein. It is, therefore, an aspect of the invention to devise screening methods to identify compounds that stimulate (agonists) or that inhibit (antagonists) the function of the polypeptide, such as agonists, antagonists and inhibitors. Accordingly, in a further aspect, the present invention provides for a method of screening compounds to identify those that stimulate or inhibit the function of the polypeptide. In general, agonists or antagonists may be employed for therapeutic and prophylactic purposes for the Diseases mentioned herein mentioned. Compounds may be identified from a variety of sources, for example, cells, cell-free preparations, chemical libraries, and natural product mixtures. Such agonists and antagonists so-identified may be natural or modified substrates, ligands, receptors, enzymes, etc., as the case may be, of the polypeptide; or may be structural or functional mimetics thereof (see Coligan, et al., CURRENT PROTOCOLS IN IMMUNOLOGY 1(2): Chapter 5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, a screening method may involve measuring or, qualitatively or quantitatively, detecting the competition of binding of a candidate compound to the polypeptide with a labeled competitor (e.g., agonist or antagonist). Further, screening methods may test whether the candidate compound results in a signal generated by an agonist or antagonist of the polypeptide, using detection systems appropriate to cells bearing the polypeptide. Antagonists are generally assayed in the presence of a known agonist and an effect on activation by the agonist by the presence of the candidate compound is observed. Further, screening methods may simply comprise the steps of mixing a candidate compound with a solution comprising a polypeptide of the present invention, to form a mixture, measuring mouse mASP1 activity in the mixture, and comparing a mouse mASP1 activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well microtiter plates but also emerging methods such as the nanowell method described by Schullek, et al., *Anal Biochem.,* 30 246, 20–29, (1997).

Fusion proteins, such as those made from Fc portion and mouse mASP1 polypeptide, as herein described, can also be used for high-throughput screening assays to identify antagonists of antagonists of the polypeptide of the present invention (see D. Bennett, et al., *J. Mol. Recognition,* 8:52–58 (1995); and K. Johanson, et al., *J. Biol. Chem.,* 270(16):9459–9471 (1995)).

Examples of potential polypeptide antagonists include antibodies or, in some cases, oligopeptides or proteins that are closely related to ligands, substrates, receptors, enzymes, etc., as the case may be, of a mASP1 polypeptide, e.g., a fragment of a ligand, substrate, receptor, enzyme, etc.; or small molecules which bind to a mASP1 polypeptide but do not elicit a response, so that an activity of a mASP1 polypeptide is prevented.

Thus, in another aspect, the present invention relates to a screening kit for identifying agonists, antagonists, inhibitors, ligands, receptors, substrates, enzymes, etc. for polypeptides of the present invention; or compounds which decrease or enhance the production of such polypeptides, which compounds comprise a member selected from the group consisting of:

(a) a polypeptide of the present invention;

(b) a recombinant cell expressing a polypeptide of the present invention; or (c) a cell membrane expressing a polypeptide of the present invention; which polypeptide is preferably that of SEQ ID NO: 2.

It will be appreciated that in any such kit, (a), (b) or (c) may comprise a substantial component.

It will also be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;

(b) deducing the three-dimensional structure for the likely reactive or binding site(s) of an agonist, antagonist or inhibitor;

(c) synthesizing candidate compounds that are predicted to bind to or react with the deduced binding or reactive site; and (d) testing whether the candidate compounds are indeed agonists, antagonists or inhibitors.

It will be further appreciated that this will normally be an iterative process.

In an alternative preferred embodiment, the present invention relates to the use of mouse mASP1 polypeptides, polynucleotides, and recombinant materials thereof in selection screens to identify compounds which are neither agonists nor antagonist/inhibitors of mouse mASP1. The data from such a selection screen is expected to provide in vitro and in vivo comparisons and to predict oral absorption, pharmacokinetics in humans. The ability to make such a comparison of data will enhance formulation design through the identification of compounds with optimal development characteristics, ie., high oral bioavailability, UID (once a day) dosing, reduced drug interactions, reduced variability, and reduced food effects, among others.

The following definitions are provided to facilitate understanding of certain terms used frequently herein.

"Allele" refers to one or more alternative forms of a gene occurring at a given locus in the genome.

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO: 1.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses, it would be desirable to be able to delete the Fc part after the fusion protein has been expressed, detected, and purified.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms, "ortholog", and "paralog". "Ortholog" refers to polynucleotides/genes or polypeptide that are homologs via speciation, that is closely related and assumed to have commend descent based on structural and functional considerations. "Paralog" refers to polynucleotides/genes or polypeptide that are homologs via gene duplication, for instance, duplicated variants within a genome.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared. For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated 'score' from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J., et al, *Nucleic*

*Acids Res,* 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J. Mol. Biol., 147:195–197, 1981, Advances in Applied Mathematics, 2, 482489, 1981) and finds the best single region of similarity between two sequences. BEST-FIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (*J. Mol Biol.,* 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S. F., et al., *J. Mol. Biol.,* 215, 403–410, 1990, Altschul S. F., et al., Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183: 63–99 (1990); Pearson W R and Lipman D. J., Proc Nat Acad Sci USA, 85: 2444–2448 (1988) (available as part of the Wisconsin Sequence Analysis Package).

Preferably, the BLOSUM62 amino acid substitution matrix (Henikoff S. and Henikoff J. G., *Proc. Nat. Acad. Sci. USA,* 89: 10915–10919 (1992)) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value, as hereinbefore described.

Alternatively, for instance, for the purposes of interpreting the scope of a claim including mention of a "% identity" to a reference polynucleotide, a polynucleotide sequence having, for example, at least 95% identity to a reference polynucleotide sequence is identical to the reference sequence except that the polynucleotide sequence may include up to five point mutations per each 100 nucleotides of the reference sequence. Such point mutations are selected from the group consisting of at least one nucleotide deletion, substitution, including transition and transversion, or insertion. These point mutations may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having at least 95% identity to a reference polynucleotide sequence, up to 5% of the nucleotides of the in the reference sequence may be deleted, substituted or inserted, or any combination thereof, as hereinbefore described. The same applies *mutatis mutandis* for other % identities such as 96%, 97%, 98%, 99% and 100%.

For the purposes of interpreting the scope of a claim including mention of a "% identity" to a reference polypeptide, a polypeptide sequence having, for example, at least 95% identity to a reference polypeptide sequence is identical to the reference sequence except that the polypeptide sequence may include up to five point mutations per each 100 amino acids of the reference sequence. Such point mutations are selected from the group consisting of at least one amino acid deletion, substitution, including conservative and non-conservative substitution, or insertion. These point mutations may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a sequence polypeptide sequence having at least 95% identity to a reference polypeptide sequence, up to 5% of the amino acids of the in the reference sequence may be deleted, substituted or inserted, or any combination thereof, as hereinbefore described. The same applies *mutatis mutandis* for other % identities such as 96%, 97%, 98%, 99%, and 100%.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 95, 97 or 100% identity to the reference sequence of SEQ ID NO: 1, wherein said polynucleotide sequence may be identical to the reference sequence of SEQ ID NO: 1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO: 1 by the integer defining the percent identity divided by 100 and then subtracting that product from said total number of nucleotides in SEQ ID NO: 1, or:

$$n_n \leq x_n - (x_n \cdot y),$$

wherein $n_n$ is the number of nucleotide alterations, $x_n$ is the total number of nucleotides in SEQ ID NO: 1, y is 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO: 2 may create nonsense, missense or frameshift mutations in this coding sequence and thereby alter the polypeptide encoded by the polynucleotide following such alterations.

(2) Polypeptide embodiments further include an isolated polypeptide comprising a polypeptide having at least a 95, 97 or 100% identity to a polypeptide reference sequence of SEQ ID NO: 2, wherein said polypeptide sequence may be identical to the reference sequence of SEQ ID NO: 2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO: 2 by the integer defining the percent identity divided by 100 and then subtracting that product from said total number of amino acids in SEQ ID NO: 2, or:

$$n_a \leq x_a - (x_a \cdot y)$$

wherein $n_a$ is the number of amino acid alterations, $x_a$ is the total number of amino acids in SEQ ID NO: 2, y is 0.95 for 95%, 0.97 for 97% or 1.00 for 100%, and y is the symbol for the multiplication operator, and wherein any non-integer product of $x_a$ and y is rounded down to the nearest integer prior to subtracting it from $x_a$.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Knock-in" refers to the fusion of a portion of a wild-type gene to the cDNA of a heterologous gene "Knock-out" refers to partial or complete suppression of the expression of a protein encoded by an endogenous DNA sequence in a cell. The "knock-out" can be affected by targeted deletion of the whole or part of a gene encoding a protein, in an embryonic stem cell. As a result, the deletion may prevent or reduce the expression of the protein in any cell in the whole animal in which it is normally expressed.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Transgenic animal" refers to an animal to which exogenous DNA has been introduced while the animal is still in its embryonic stage. In most cases, the transgenic approach aims at specific modifications of the genome, e.g., by introducing whole transcriptional units into the genome, or by up- or down-regulating pre-existing cellular genes. The targeted character of certain of these procedures sets transgenic technologies apart from experimental methods in which random mutations are conferred to the germline, such as administration of chemical mutagens or treatment with ionizing solution.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs comprising one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may comprise amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may comprise many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS—STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors", *Meth. Enzmol.*

(1990) 182:626–646 and Rattan, et al., "Protein Synthesis: Post-translational Modifications and Aging", *Ann NY Acad Sci* (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

All publications including, but not limited to, patents and patent applications, cited in this specification or to which this patent application claims priority, are herein incorporated by reference as if each individual publication were specifically and individually indicated to be incorporated by reference herein as though fully set forth.

| SEQUENCE INFORMATION | |
|---|---|
| ATGGGCGCGCTGCTTCGAGCACTCTTGCTCCTGGTGCTGGCGCAGTGGCTCTTGAGTGCGGTCCCCGCGCTGGC | SEQ ID NO:1 |
| CCCCGCGCCCTTCACGCTGCCCCTCCAAGTGGCCGGGGCCACGAACCACAGAGCCTCGGCTGTTCCCGGACTCG | |
| GGACCCCCGAGTTGCCCCGGGCCGATGGTCTGGCCCTCGCACTGGAGCCTGTCAGGGCTACTGCCAACTTCTTG | |
| GCTATGGTGGACAACCTTCAGGGGACTCTGGCCGCGGCTACTACCTAGAGATGCTGATCGGGACCCCTCCGCA | |
| GAAGGTACAGATTCTTGTGGACACTGGAAGCAGTAACTTCGCTGTGGCAGGTGCCCCACACTCCTACATAGACA | |
| CCTACTTTGACTCAGAGAGCTCCAGCACATACCACTCCAAGGGCTTTGATGTCACTGTGAAGTACACACAGGGA | |
| AGCTGGACTGGCTTTGTTGGTGAGGACCTTGTCACCATCCCAAAAGGCTTCAACAGCTCTTTCTTGGTCAATAT | |
| TGCCACTATTTTCGAGTCTGAGAATTTCTTTTTGCCTGGTATTAAATGGAATGGAATCCTTGGACTTGCTTATG | |
| CTGCTTTGGCCAAGCCATCAAGCTCTCTGGAGACATTTTTTGATTCCCTGGTGGCCCAAGCAAAGATTCCAGAC | |
| ATTTTCTCCATGCAGATGTGCGGGGCTGGATTGCCAGTAGCTGGTTCTGGTACCAACGGAGGTAGTCTTGTCCT | |
| GGGTGGGATTGAACCAAGTTTGTATAAAGGAGATATCTGGTATACCCCAATTAAAGAGGAATGGTACTATCAAA | |
| TAGAAATCCTGAAGTTGGAAATTGGAGGCCAGAACCTCAACCTGGACTGCAGAGAGTATAACGCAGACAAGGCC | |
| ATTGTGGACAGTGGCACCACGCTCCTGCGCCTGCCCCAGAAGGTGTTTGATGCAGTGGTGGAAGCTGTGGCACG | |
| AACATCTCTGATTCCAGAGTTTTCTGATGGCTTCTGGACAGGGGCCCAGCTGGCATGCTGGACAAATTCTGAAA | |
| CGCCATGGGCATATTTCCCTAAGATTTCTATCTACCTGAGAGATGAGAATGCCAGTCGCTCCTTCCGGATCACC | |
| ATTCTCCCACAGCTCTACATTCAGCCCATGATGGGAGCTGGTTTCAATTATGAATGCTACCGTTTTGGTATCTC | |
| CTCTTCCACAAATGCGCTGGTGATTGGTGCGACCGTGATGGAAGGCTTCTACGTGGTCTTTGACAGAGCTCAGA | |
| GGAGGGTGGGCTTTGCAGTGAGTCCCTGTGCAGAGATTGAAGGTACCACAGTGTCTGAAATTTCTGGGCCCTTT | |
| TCCACGGAAGACATAGCCAGCAACTGTGTTCCAGCACAGGCTCTGAATGAGCCCATCTTGTGGATTGTGTCCTA | |
| TGCCCTGATGAGTGTGTGTGGAGCCATTCTCCTGGTTCTGATCCTCCTCCTGCTGCTCCCGCTGCACTGCCGTC | |
| ATGCCCCCCGAGACCCTGAGGTAGTTAACGATGAGTCCTCACTAGTCAGACATCGCTGGAAATGA | |
| MGALLRALLLLVLAQWLLSAVPALAPAPFTLPLQVAGATNHRASAVPGLGTPELPRADGLALALEPVRATANFL | SEQ ID NO:2 |
| AMVDNLQGDSGRGYYLEMLIGTPPQKVQILVDTGSSNFAVAGAPHSYIDTYFDSESSSTYHSKGFDVTVKYTQG | |
| SWTGFVGEDLVTIPKGFNSSFLVNIATIFESENFFLPGIKWNGILGLAYAALAKPSSSLETFFDSLVAQAKIPD | |

SEQUENCE INFORMATION

IFSMQMCGAGLPVAGSGTNGGSLVLGGIEPSLYKGDIWYTPIKEEWYYQIEILKLEIGGQNLNLDCREYNADKA
IVDSGTTLLRLPQKVFDAVVEAVARTSLIPEFSDGFWTGAQLACWTNSETPWAYFPKISIYLRDENASRSFRIT
ILPQLYIQPMMGAGFNYECYRFGISSSTNALVIGATVMEGFYVVFDRAQRRVGFAVSPCAEIEGTTVSEISGPF
STEDIASNCVPAQALNEPILWIVSYALMSVCGAILLVLILLLLLPLHCRHAPRDPEVVVDESSLVRHRWK

What is claimed is:

1. An isolated polynucleotide comprising the nucleotide sequence set forth in SEQ ID NO: 1.

2. The isolated polynucleotide of claim 1 consisting of the nucleotide sequence set forth in SEQ ID NO: 1.

3. An isolated polynucleotide that encodes a polypeptide comprising the amino acid sequence set forth in SEQ ID NO: 2.

4. The isolated polynucleotide of claim 3 wherein the polynucleotide encodes the amino acid sequence set forth in SEQ ID NO: 2.

5. An expression vector comprising the isolated polynucleotide of claim 3 when said expression vector is present in a compatible host cell.

6. An isolated host cell comprising the expression vector of claim 5.

7. A process for producing a mASP1 polypeptide comprising culturing the host cell of claim 6 and recovering the polypeptide from the culture.

8. A membrane of the host cell of claim 6 expressing said polypeptide.

* * * * *

SEQUENCE LISTING

<160> NUMBER OF SEQ ID NOS: 2

<210> SEQ ID NO 1
<211> LENGTH: 1545
<212> TYPE: DNA
<213> ORGANISM: MUS MUSCULUS

<400> SEQUENCE: 1

| | | | | | |
|---|---|---|---|---|---|
| atgggcgcgc | tgcttcgagc | actcttgctc | ctggtgctgg | cgcagtggct | cttgagtgcg | 60 |
| gtcccccgcg | tggcccccgc | gcccttcacg | ctgcccctcc | aagtggccgg | ggccacgaac | 120 |
| cacagagcct | cggctgttcc | cggactcggg | accccgagt | tgccccgggc | cgatggtctg | 180 |
| gccctcgcac | tggagcctgt | cagggctact | gccaacttct | tggctatggt | ggacaacctt | 240 |
| caggggagct | ctggccgcgg | ctactaccta | gagatgctga | tcgggacccc | tccgcagaag | 300 |
| gtacagattc | ttgtggacac | tggaagcagt | aacttcgctg | tggcaggtgc | ccacactcc | 360 |
| tacatagaca | cctactttga | ctcagagagc | tccagcacat | accactccaa | gggctttgat | 420 |
| gtcactgtga | agtacacaca | gggaagctgg | actggctttg | ttggtgagga | ccttgtcacc | 480 |
| atcccaaaag | gcttcaacag | ctctttcttg | gtcaatattg | ccactatttt | cgagtctgag | 540 |
| aatttctttt | tgcctggtat | taaatggaat | ggaatccttg | gacttgctta | tgctgctttg | 600 |
| gccaagccat | caagctctct | ggagacattt | tttgattccc | tggtggccca | agcaaagatt | 660 |
| ccagacattt | tctccatgca | gatgtgcggg | gctggattgc | cagtagctgg | ttctggtacc | 720 |
| aacggaggta | gtcttgtcct | gggtgggatt | gaaccaagtt | tgtataaagg | agatatctgg | 780 |
| tatccccaa | ttaaagagga | gatggtactat | caaatagaaa | tcctgaagtt | ggaaattgga | 840 |
| ggccagaacc | tcaacctgga | ctgcagagag | tataacgcag | acaaggccat | tgtggacagt | 900 |
| ggcaccacgc | tcctgcgcct | gccccagaag | gtgtttgatg | cagtggtgga | agctgtggca | 960 |
| cgaacatctc | tgattccaga | gttttctgat | ggcttctgga | caggggccca | gctggcatgc | 1020 |
| tggacaaatt | ctgaaacgcc | atgggcatat | ttccctaaga | tttctatcta | cctgagagat | 1080 |
| gagaatgcca | gtcgctcctt | ccggatcacc | attctcccac | agctctacat | tcagcccatg | 1140 |
| atgggagctg | gtttcaatta | tgaatgctac | cgttttggta | tctcctcttc | cacaaatgcg | 1200 |
| ctggtgattg | gtgcgaccgt | gatggaaggc | ttctacgtgg | tctttgacag | agctcagagg | 1260 |
| agggtgggct | ttgcagtgag | tccctgtgca | gagattgaag | gtaccacagt | gtctgaaatt | 1320 |
| tctgggccct | tttccacgga | agacatagcc | agcaactgtg | ttccagcaca | ggctctgaat | 1380 |
| gagcccatct | tgtggattgt | gtcctatgcc | ctgatgagtg | tgtgtggagc | cattctcctg | 1440 |
| gttctgatcc | tcctcctgct | gctcccgctg | cactgccgtc | atgcccccg | agaccctgag | 1500 |
| gtagttaacg | atgagtcctc | actagtcaga | catcgctgga | aatga | | 1545 |

<210> SEQ ID NO 2
<211> LENGTH: 514
<212> TYPE: PRT
<213> ORGANISM: MUS MUSCULUS

<400> SEQUENCE: 2

Met Gly Ala Leu Leu Arg Ala Leu Leu Leu Val Leu Ala Gln Trp
1               5                   10                  15

Leu Leu Ser Ala Val Pro Ala Leu Ala Pro Ala Pro Phe Thr Leu Pro
                20                  25                  30

Leu Gln Val Ala Gly Ala Thr Asn His Arg Ala Ser Ala Val Pro Gly
                35                  40                  45

Leu Gly Thr Pro Glu Leu Pro Arg Ala Asp Gly Leu Ala Leu Ala Leu
    50                  55                  60

Glu Pro Val Arg Ala Thr Ala Asn Phe Leu Ala Met Val Asp Asn Leu
65                  70                  75                  80

Gln Gly Asp Ser Gly Arg Gly Tyr Tyr Leu Glu Met Leu Ile Gly Thr
                85                  90                  95

Pro Pro Gln Lys Val Gln Ile Leu Val Asp Thr Gly Ser Ser Asn Phe
                100                 105                 110

Ala Val Ala Gly Ala Pro His Ser Tyr Ile Asp Thr Tyr Phe Asp Ser
                115                 120                 125

Glu Ser Ser Ser Thr Tyr His Ser Lys Gly Phe Asp Val Thr Val Lys
130                 135                 140

Tyr Thr Gln Gly Ser Trp Thr Gly Phe Val Gly Glu Asp Leu Val Thr
145                 150                 155                 160

Ile Pro Lys Gly Phe Asn Ser Ser Phe Leu Val Asn Ile Ala Thr Ile
                165                 170                 175

Phe Glu Ser Glu Asn Phe Phe Leu Pro Gly Ile Lys Trp Asn Gly Ile
                180                 185                 190

Leu Gly Leu Ala Tyr Ala Ala Leu Ala Lys Pro Ser Ser Ser Leu Glu
                195                 200                 205

Thr Phe Phe Asp Ser Leu Val Ala Gln Ala Lys Ile Pro Asp Ile Phe
    210                 215                 220

Ser Met Gln Met Cys Gly Ala Gly Leu Pro Val Ala Gly Ser Gly Thr
225                 230                 235                 240

Asn Gly Gly Ser Leu Val Leu Gly Gly Ile Glu Pro Ser Leu Tyr Lys
                245                 250                 255

Gly Asp Ile Trp Tyr Thr Pro Ile Lys Glu Glu Trp Tyr Tyr Gln Ile
                260                 265                 270

Glu Ile Leu Lys Leu Glu Ile Gly Gly Gln Asn Leu Asn Leu Asp Cys
                275                 280                 285

Arg Glu Tyr Asn Ala Asp Lys Ala Ile Val Asp Ser Gly Thr Thr Leu
    290                 295                 300

Leu Arg Leu Pro Gln Lys Val Phe Asp Ala Val Val Glu Ala Val Ala
305                 310                 315                 320

Arg Thr Ser Leu Ile Pro Glu Phe Ser Asp Gly Phe Trp Thr Gly Ala
                325                 330                 335

Gln Leu Ala Cys Trp Thr Asn Ser Glu Thr Pro Trp Ala Tyr Phe Pro
                340                 345                 350

Lys Ile Ser Ile Tyr Leu Arg Asp Glu Asn Ala Ser Arg Ser Phe Arg
                355                 360                 365

Ile Thr Ile Leu Pro Gln Leu Tyr Ile Gln Pro Met Met Gly Ala Gly

-continued

```
            370                 375                 380
Phe Asn Tyr Glu Cys Tyr Arg Phe Gly Ile Ser Ser Ser Thr Asn Ala
385                 390                 395                 400

Leu Val Ile Gly Ala Thr Val Met Glu Gly Phe Tyr Val Val Phe Asp
                405                 410                 415

Arg Ala Gln Arg Arg Val Gly Phe Ala Val Ser Pro Cys Ala Glu Ile
                420                 425                 430

Glu Gly Thr Thr Val Ser Glu Ile Ser Gly Pro Phe Ser Thr Glu Asp
                435                 440                 445

Ile Ala Ser Asn Cys Val Pro Ala Gln Ala Leu Asn Glu Pro Ile Leu
                450                 455                 460

Trp Ile Val Ser Tyr Ala Leu Met Ser Val Cys Gly Ala Ile Leu Leu
465                 470                 475                 480

Val Leu Ile Leu Leu Leu Leu Leu Pro Leu His Cys Arg His Ala Pro
                485                 490                 495

Arg Asp Pro Glu Val Val Asn Asp Glu Ser Ser Leu Val Arg His Arg
                500                 505                 510

Trp Lys
```